United States Patent [19]

Antfang et al.

[11] Patent Number: 5,326,573

[45] Date of Patent: * Jul. 5, 1994

[54] COATED GRANULES CONTAINING LIQUID AND SOLID ACTIVE COMPOUNDS

[75] Inventors: Elmar Antfang, Monheim; Dimitrios Kerimis, Cologne; Rolf-Jürgen Singer, Wuppertal, all of Fed. Rep. of Germany

[73] Assignee: Bayer Aktiengesellschaft, Leverkusen, Fed. Rep. of Germany

[ * ] Notice: The portion of the term of this patent subsequent to Sep. 10, 2008 has been disclaimed.

[21] Appl. No.: 23,418

[22] Filed: Feb. 23, 1993

Related U.S. Application Data

[63] Continuation of Ser. No. 461,207, Jan. 5, 1990, abandoned.

[30] Foreign Application Priority Data

Jan. 18, 1989 [DE] Fed. Rep. of Germany ....... 3901274

[51] Int. Cl.$^5$ ................................................ A61K 9/58
[52] U.S. Cl. .......................... 424/490; 71/DIG. 1; 424/405; 424/407; 424/408; 424/409; 424/417; 424/419; 424/421; 424/489; 424/497; 428/403; 428/404; 428/405; 428/407; 514/769; 514/770; 514/772.2; 514/772.3
[58] Field of Search ............... 424/405, 407, 417, 421, 424/489, 490, 497, 408, 409, 419; 514/772.2, 772.3, 770, 769; 428/403, 404, 405, 407; 71/DIG. 1

[56] References Cited

U.S. PATENT DOCUMENTS

| | | | |
|---|---|---|---|
| 3,137,618 | 6/1964 | Pearce | 424/421 |
| 3,980,463 | 9/1976 | Muramoto et al. | 424/417 X |
| 4,110,499 | 8/1978 | Harrison | 428/325 X |
| 4,230,809 | 10/1980 | Heinrich et al. | 424/419 X |
| 4,309,538 | 1/1982 | Schmidt et al. | 544/182 |
| 4,474,852 | 10/1984 | Craig | 428/403 |
| 4,711,659 | 12/1987 | Moore | 71/93 |
| 4,798,766 | 1/1989 | Rice | 428/404 |
| 4,837,321 | 6/1989 | Kerimis et al. | 544/193 |
| 4,900,551 | 2/1990 | Ohtsubo et al. | 424/419 |
| 4,902,340 | 2/1990 | Hubele | 71/65 |
| 4,925,482 | 5/1990 | Stroech et al. | 71/76 |
| 4,945,000 | 7/1990 | Widdmann et al. | 428/407 |
| 5,047,243 | 9/1991 | Antfang et al. | 424/408 |
| 5,169,644 | 12/1992 | Molls et al. | 424/497 |

FOREIGN PATENT DOCUMENTS

| | | |
|---|---|---|
| 0016278 | 1/1980 | European Pat. Off. . |
| 0192118 | 8/1986 | European Pat. Off. . |
| 0230601 | 8/1987 | European Pat. Off. . |

*Primary Examiner*—Thurman K. Page
*Assistant Examiner*—Robert H. Harrison
*Attorney, Agent, or Firm*—Sprung Horn Kramer & Woods

[57] ABSTRACT

In the combating of agricultural and horticultural pests by applying to a locus from which it is desired to exclude such pests a normally liquid active compound and a normally solid active compound, the improvement which comprises applying such active compound in the form of granules comprising a) carrier granules having a non-absorptive surface, b) at least one liquid active compound and at least one solid active compound, c) at least one adhesive based on polyurethane as a binder, optionally mixed with a further adhesive selected from the group consisting of polyvinyl acetate, polyvinylpyrrolidine, polyvinyl alcohol, vinyl acetate/di-n-butyl maleate copolymers, acrylic acid ester, vinyl acetate/ethylene, vinyl acetate/ethylene/vinyl chloride, vinyl acetate/acrylic acid ester, vinyl acetate/vinyl ester and styrene/acrylic acid ester, and d) optionally an additive.

11 Claims, No Drawings

COATED GRANULES CONTAINING LIQUID AND SOLID ACTIVE COMPOUNDS

This application is a continuation of application Ser. No. 461,207, filed Jan. 5, 1990, now abandoned.

The present invention relates to new coated granules containing liquid and solid active compounds (so-called "coated combination granules"). According to the invention, active compounds are preferably taken to mean the active components from the field of plant protection, such as insecticides, nematicides, acaricides, fungicides, herbicides and growth regulators.

The invention furthermore relates to a process for the preparation of the new coated combination granules and to their use for controlling pests, preferably in the field of agriculture and gardening.

There is already known a large number of coated granules which contain solid or liquid biocidal active compounds on a granular carrier (cf. Büchel, "Pflanzenschutz und Schädlingsbekämpfung [Plant Protection and Pest Control]", Georg-Thieme Verlag, Stuttgart, 1977, pages 198 and 199).

For example, coated granules with solid active compounds can be prepared by affixing the active components, if appropriate in a mixture with additives, in a finely-divided form to the compact or non-absorptive surface of the carrier, with the aid of a range of adhesives.

Coated granules which contain liquid biocidal active compounds can be prepared for example by soaking porous or absorptive carriers in liquid active compounds or in solutions of liquid active compounds in suitable solvents, in each case optionally in a mixture with additives. Coated granules can only be prepared by this method when a suitable solvent for dissolving the solid active-compound component is available. In addition to this restriction, the properties of these granules are not always satisfactory. By virtue of the low hardness of the absorptive granules, physical forces may result in abrasion, and in this way the granules can liberate dust which contains biocides.

New coated granules containing liquid and solid active compounds have now been found, which contain a) a granular carrier having a non-absorptive surface, b) at least one liquid active compound besides a solid one, c) as the binder, at least one adhesive on a polyurethane basis, if appropriate in a mixture with another adhesive on the basis of one of the following systems: polyvinyl acetate, polyvinylpyrrolidone, polyvinyl alcohol, vinyl acetate/di-n-butyl- maleate copolymers, acrylic esters, vinyl acetate/ethylene, vinyl acetate/ethylene/vinyl chloride, vinyl acetate/acrylic esters, vinyl acetate/vinyl esters, styrene/acrylic esters, as well as d) if appropriate, additives.

Furthermore, it has been found that the coated combination granules according to the invention can be prepared by a process in which in a mixer, a granular carrier having a non-absorptive surface is sprayed with an aqueous dispersion of a polyurethane adhesive, if appropriate with the addition of a thickener and if appropriate in a mixture with an aqueous dispersion of another adhesive on the basis of one of the following systems: polyvinyl acetate, polyvinylpyrrolidone, polyvinyl alcohol, vinyl acetate/di-n-butyl maleate copolymers, acrylic esters, vinyl acetate/ethylene, vinyl acetate/ethylene/vinyl chloride, vinyl acetate/acrylic esters, vinyl acetate/vinyl esters and styrene/acrylic esters, followed by the addition of a premixture containing the liquid active compound and a mixture containing the solid active compound and if appropriate extenders, this, if appropriate, being sprayed again with an aqueous dispersion of a polyurethane adhesive, if appropriate in a mixture with an aqueous dispersion of another adhesive on the basis of the abovementioned systems, and the resulting granular products are dried.

Finally, it has been found that the coated combination granules according to the invention can be used for a wide range of purposes in agriculture and in horticulture, depending on the active compounds contained.

It must be considered as extremely surprising that the coated combination granules according to the invention show a better activity than granules which are already known, in which liquid active compounds, or combinations of liquid and solid active compounds, in the form of a solution, are absorbed onto porous or absorptive carriers. It is furthermore advantageous that the polyurethane compounds which are used as adhesives are readily degraded under environmental conditions and release the active compound, but protect the active compound from chemical influences until it is released.

The coated combination granules according to the invention are distinguished by a series of advantages. The advantage of the coated combination granules is a simultaneous application of solid and liquid biocidal active compounds.

Furthermore, the active compounds contained in these granules are released at their site of application in the specific desired way. Moreover, the coated combination granules according to the invention are products which are distinguished by an extremely high resistance to abrasion.

In the present case, the products according to the invention are designated as coated combination granules, the coated combination granules containing at least one liquid optionally in form of micorencapsulation and one solid compound.

Carriers having a non-absorptive surface which can be employed in the coated combination granules according to the invention are all customary carriers which are contained in granules of this type and which have a non-absorptive surface. Calcite, dolomite and sand, such as, for example, quartz sand, are preferably suitable.

The mean particle diameter of the carriers can be varied within a certain range. In general, the mean particle diameter is between 0.1 and 3.0 mm, preferably between 0.3 and 1 mm.

In the present case, active-compound components are all active compounds which can customarily be used in plant protection, as already mentioned above. These preferably include insecticides, nematicides, acaricides, fungicides, herbicides and growth regulators.

The granules according to the invention contain at least one active compound which is liquid at room temperature and one active compound which is solid at room temperature.

Suitable active compounds which are solid at room temperature are preferably carbamates, nitromethylenes, nitroimino derivatives, pyrethroids and phenylpyrazoles. The following may be mentioned by way of example:

2-isopropoxy-phenyl N-methyl-carbamate, 2,3-dihydro-2,2-dimethyl-7-benzofuranyl N-methyl-carbamate, 3,5-dimethyl-4-methylthio-phenyl N-methyl-carbamate, 2-(1-methylethyl)phenyl methyl carbamate, 1-(2-chloro-5-pyridinyl-methyl)-2-nitroiminoimidazolidine.

Suitable biocidal active compounds which are liquid at room temperature are preferably phosphoric acid derivatives. The following may be mentioned by way of example:

O-ethyl O-(2-isopropyloxycarbonyl-phenyl) W-isopropylthionophosphoramidate,

O,O-diethyl α-cyanobenzylideneamino-oxyphosphonothioates,

O,O-diemethyl O-(4-methylmercapto-3-methyl-phenyl) thionophosphate,

O-ethyl O-(4-methylthio-phenyl) S-propyl dithiophosphate, (O,O-diethyl-thionophosphoryl)-α-oximino-phenylacetonitrile, O,O-diethyl O-(3-chloro-4-methyl-7-coumarinyl) thiophosphate, 5-[1,2-bis-(ethoxycarbonyl)-ethyl] O,O-dimethyl dithiophosphate.

The binder used in the coated combination granules according to the invention is an adhesive on a polyurethane basis, if appropriate in a mixture with another adhesive on the basis of one of the following systems: polyvinyl acetate, polyvinylpyrrolidone, polyvinyl alcohol, as well as with copolymers of vinyl acetate/din-butyl maleate, acrylic esters, vinyl acetate/ethylene, vinyl acetate/ethylene/vinyl chloride, vinyl acetate/acrylic esters, vinyl acetate/vinyl esters and styrene/acrylic esters.

Additives which may be present in the coated combination granules according to the invention are extenders, grinding auxiliaries, colorants as well as water and organic solvents.

Suitable extenders in this context are preferably finely-divided inorganic solids, such as ground natural minerals, for example kaolin, clays, talc, chalk, quartz powder, attapulgite, montmorillonite, sepiolite, zeolite, bentonite, furthermore meals of synthetic minerals, such as highly-disperse silicic acids.

Suitable grinding auxiliaries are all customary substances which can be used for this purpose. Kaolin, clays, talc, chalk and quartz powder may preferably be mentioned.

Colorants which are suitable as additives and which may be mentioned are inorganic pigments, such as iron oxide, titanium dioxide, Prussian Blue and organic dyestuffs, such as anthraquinone, azo and metal phthalocyanine dyestuffs.

Possible organic solvents are all organic solvents which can customarily be used for the preparation of coated granules. Low-boiling organic solvents, such as methanol, ethanol, butanol and methylene chloride are preferably suitable.

The granules according to the invention consist of granular carriers on whose non-absorptive surface there is a coating which contains at least one liquid biocidal active compound and one solid biocidal active compound. Polyurethane and mixtures of polyurethane and polyvinyl acetate, polyvinylpyrrolidone, polyvinyl alcohol, as well as mixtures with copolymers of vinyl acetate/di-n-butyl maleate, acrylic esters, vinyl acetate/ethylene, vinyl acetate/ethylene/vinyl chloride, vinyl acetate/acrylic esters, vinyl acetate/vinyl esters, styrene/acrylic esters are active as binders, which, if appropriate, can contain additives. The components present in the coating can also penetrate into indentations in the carrier in some cases.

The percentages of the components contained in the coated combination granules according to the invention can be varied within a substantial range. The proportion of granular carrier is generally between 50 and 99.5% by weight, preferably between 60 and 92% by weight. The proportion of liquid and of solid biocidal active compounds is generally between 0.1 and 20% by weight, preferably between 0.5 and 15% by weight.

The proportion of polyurethane acting as the binder and of mixtures of polyurethane and polyvinyl acetate, polyvinylpyrrolidone and polyvinyl alcohol, as well as mixtures with copolymers of vinyl acetate/di-n-butyl maleate, acrylic esters, vinyl acetate/ethylene, vinyl acetate/ethylene/vinyl chloride, vinyl acetate/acrylic esters, vinyl acetate/vinyl esters and styrene/acrylic esters is generally between 0.1 and 4% by weight, preferably between 0.3 and 3% by weight, in general 0.05 to 0.49 part by weight, preferably 0.1 to 0.2 part by weight, of polyvinyl acetate, polyvinylpyrrolidone, polyvinyl alcohol as well as amounts of the abovementioned copolymers being present per part of polyurethane. If appropriate, additives are present in amounts of 1 to 40 parts by weight, preferably of 2 to 30 parts by weight.

In the preparation of the coated combination granules according to the invention, it is preferred to use all those components which have already been mentioned in connection with the description of the coated combination granules according to the invention as being preferred.

In the preparation of the granules according to the invention, it is necessary to employ the solid biocidal active compounds in finely-divided form. For this purpose, the biocidal active compounds which are solid at room temperature are generally used in the finely-ground state, if appropriate in a mixture with grinding auxiliaries. The biocidal active compounds which are liquid at room temperature are generally used in a mixture with extenders, such as attapulgite, montmorillonite, sepiolite or highly-disperse silicic acid. However, it is also possible in the case of coated combination granules to employ a mixture of liquid and solid biocidal active compounds in the finely-divided state, if appropriate in a mixture with grinding auxiliaries.

Polyurethane, which acts as a binder (adhesive), or the mixture of polyurethane and those components which have already been mentioned in connection with the description of the coated combination granules according to the invention as being preferred, is employed as an aqueous dispersion, as already indicated above. Diluents which can be used for this purpose are, besides water, also organic substances, preferably low-boiling organic solvents, such as methanol, ethanol, butanol and 1,2-dichloromethane.

When carrying out the process according to the invention, a procedure is generally followed in which a granular carrier having a non-absorptive surface is introduced into a mixer, and an aqueous dispersion of polyurethane or of a mixture of polyurethane and those components which have already been mentioned in connection with the description of the coated combination granules according to the invention is sprayed onto the carrier, with continuous mixing, followed by the addition of at least one solid biocidal active compound, if appropriate in a mixture with additives, and of at least one liquid biocidal active compound, if appropriate in a mixture with additives, or by introducing a mixture of at least one solid biocidal active compound and at least one liquid biocidal active compound, and if appropriate a mixture with additives, this being followed, if appropriate, by spraying again with an aqueous dispersion of polyurethane or a mixture of polyurethane and those components which have already been mentioned in connection with the description of the coated combination granules according to the invention as being preferred, and the resulting granular products are dried.

The sequence in which the components are applied to the carrier can be varied in a specific desired manner.

In general, the process according to the invention is carried out at room temperature. However, it is also possible to carry out the process at a slightly increased temperature.

The drying temperature can be varied within a substantial range. In general, drying is carried out at temperatures for granules between 20° C. and 70° C., preferably between 30° C. and 65° C. If appropriate, drying can be carried out under reduced pressure. Furthermore, drying can be effected either in the mixer which serves for coating the carrier, or alternatively in a separate drying apparatus.

The process according to the invention can be carried out in conventional apparatus, either batchwise or continuously.

The coated combination granules according to the invention can be employed for a wide range of purposes, depending on the active components contained. For example, they can be used for controlling animal pests, fungi and/or weeds. If they contain plant growth regulators, they can also be employed for influencing the growth of crop plants.

The coated combination granules according to the invention can be applied by customary methods, such as, for example, scattering.

Suitable adhesives on a polyurethane basis are preferably those systems in which the actual polyurethane compound is formed by polyaddition of a partially-esterified glycol or a symmetric or unsymmetric polyglycol with an excess of isocyanate, diisocyanate or polyisocyanate, in which polyaddition process free isocyanate groups are preserved as prepolymers.

It is preferred to employ polyurethanes which have been prepared from a saturated polyester, formed from adipic acid and n-butanediol-n-hexanediol, by reaction with linear isocyanates or diisocyanates, during which process free isocyanate groups are preserved.

Reaction of the resulting prepolymers with mixtures of water and emulsifiers result in chain elongation and formation of an aqueous dispersion.

The preparation of the coated combination granules according to the invention can be seen from the example which follows.

Preparation Example

In a mixer, 250.0 kg of quartz sand grains with a diameter of 0.4 to 0.8 mm are sprayed, at 20° C. and with continuous mixing, with 5.0 kg of an aqueous dispersion which contains 2.0 kg of polyurethane (prepared from adipic acid and n-butanedione-n-hexanediol and reaction with isocyanate, and further reaction of the resulting prepolymers with mixtures of water and emulsifiers).

After this, 7.62 kg of a commercially available, finely-ground pulverulent mixture containing 5.72 kg of 2,3-dihydro-2,2-dimethyl-7-benzofuranyl N-methyl-carbamate of the formula

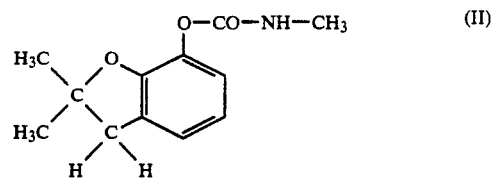

as well as 15.38 kg of a mixture of 8.58 kg of O-ethyl) O-(2-isopropyloxy-carbonyl-phenyl) N-isopropylthionophosphoramidate of the formula

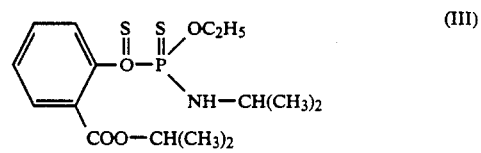

and 7.30 kg of highly-disperse silicic acid, 1.43 kg of a blue colorant as well as 1.43 kg of antistatics, are then added at room temperature.

Mixing is continued for 5 minutes at 20° C., and 5.60 kg of an aqueous polyvinyl alcohol solution which contains 0.56 kg of polyvinyl alcohol (molecular weight: $\overline{M}_w$ 26,000) is sprayed on at room temperature, with continuous mixing.

The contents of the mixer are then dried at a drying temperature of not more than 60° C., and 286.0 kg of coated combination granules having a content of active compound of the formula (II) of 2.0% by weight and of active compound of the formula (III) of 3.0% by weight are obtained in this manner.

The granules are distinguished by a very high resistance to abrasion.

Comparison Example

Coated combination granules on the basis of polyvinyl acetate/polyvinyl alcohol adhesive In a mixer, 1,265.8 kg of quartz sand grains with a diameter of 0.4 to 0.8 mm are sprayed, at room temperature and with continuous mixing, with 26.0 kg of an aqueous dispersion which contains 6.24 kg of polyvinyl acetate and 1.56 kg of polyvinyl alcohol. After this, 42.0 kg of a commercially available, finely-ground pulverulent mixture containing 31.5 kg of 2,3-dihydro-2,2-dimethyl-7-benzofuranyl N-methyl-carbamate of the formula

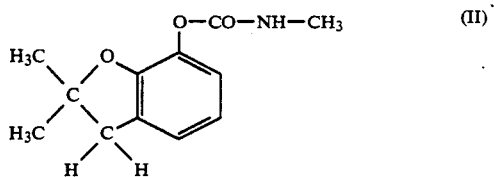

as well as a mixture of 45.9 kg of O-ethyl O-(2-isopropyloxy-carbonyl-phenyl) N-isopropylthiono-phosphoramidate of the formula

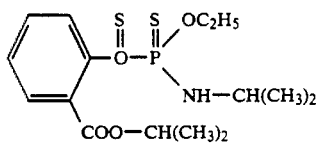

and 56.1 kg of highly-disperse silicic acid, as well as 7.2 kg of a blue colorant, are added at room temperature.

Mixing is continued for 10 minutes at room temperature, and the contents of the mixer are then dried at a drying temperature of not more than 60° C. In this manner, 1,443.0 kg of coated combination granules having a content of active compound of the formula (II) of 2.0% by weight and of active compound of the formula (III) of 3.0% by weight are obtained.

The granules obtained showed very high abrasion and softening, and were therefore not suitable for use in practice.

It is understood that the specification and examples are illustrative but not limitative of the present invention and that other embodiments within the spirit and scope of the invention will suggest themselves to those skilled in the art.

What is claimed is:

1. Coated granules from 0.1 to 3 mm in size and containing liquid and solid active compounds, comprising
   a) 50–99.5% by total weight of carrier granules having a non-absorptive surface,
   b) 0.1–20% by total weight of at least one active compound which is liquid at room temperature and at least one active compound which is solid at room temperature and which are present in finely divided form, and,
   c) 0.1–49% by total weight of at least one adhesive based on polyurethane as a binder, optionally mixed with a further adhesive selected from the group consisting of polyvinyl acetate, polyvinylpyrrolidine, polyvinyl alcohol, vinyl acetate/di-n-butyl maleate copolymer, acrylic acid ester, vinyl acetate/ethylene, vinyl acetate/ethylene/vinyl chloride, vinyl acetate/acrylic acid ester, vinyl acetate/vinyl ester and styrene/acrylic acid ester, and
   d) 1–40% by total weight of at least one additive selected from the group consisting of an extender, a grinding auxiliary, a colorant, water and an organic solvent.

2. Carrier granules according to claim 1, wherein said liquid active compound and said solid active compound are plant protection agents.

3. Carrier granules according to claim 1, wherein said liquid active compound and said solid active compound are each selected from the group consisting of insecticides, nematicides, acaricides, fungicides herbicides and growth regulators.

4. Carrier granules according to claim 1, containing as an additive an extender, colorant, water or an organic solvent.

5. Carrier granules according to claim 1, wherein said extender is a fine grain organic solid.

6. Carrier granules according to claim 1, containing a grinding auxiliary selected from the group consisting of kaolin, clay, talc, chalk and quartz powder.

7. Carrier granules according to claim 1, wherein said colorant is an inorganic pigment.

8. Carrier granules according to claim 1, containing an organic solvent selected from the group consisting of methanol, ethanol, butanol and methylene chloride.

9. A process for the preparation of carrier granules containing liquid and solid active compounds according to claim 1, comprising Spraying into a mixer granular carrier material having a non-absorptive surface and an aqueous dispersion of a polyurethane adhesive, optionally with the addition of a thickener and optionally with an aqueous dispersion of a further adhesive selected from the group consisting of polyvinyl acetate, polyvinylpyrrolidone, polyvinyl alcohol, a copolymer of vinyl acetate/di-n-butyl maleate, acrylic acid ester, vinyl acetate/ethylene, vinyl acetate/ethylene/vinyl chloride, vinyl acetate/acrylic acid ester, vinyl acetate/vinyl ester and styrene/acrylic acid ester, then adding a premixture containing the liquid active compound and a mixture containing the solid active compound and an extender, optionally again spraying the product with an aqueous dispersion of the further adhesive, and then drying the granules.

10. In the combating of agricultural and horticultural pests by applying to a locus from which it is desired to exclude such pests a normally liquid active compound and a normally solid active compound, the improvement which comprises applying said liquid active compound and said solid active compound in the form of granules according to claim 1.

11. Coated granules in accordance with claim 1 wherein said carrier granules are selected from the group consisting of calcite, dolomite and sand.

* * * * *